Figure 1:
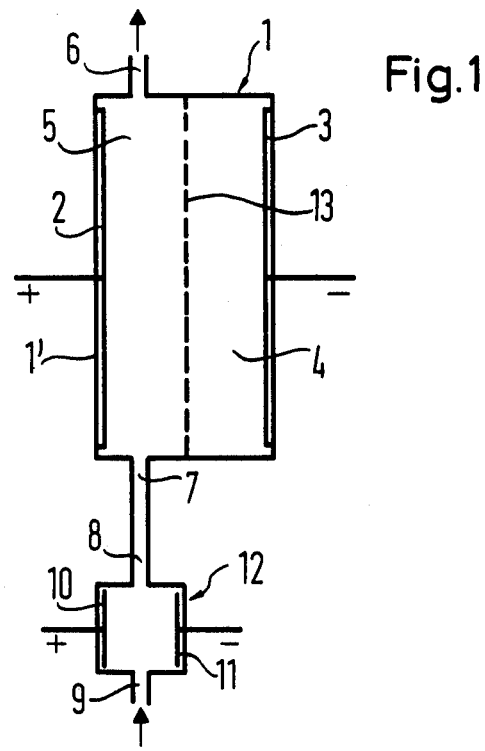
Figure 2:
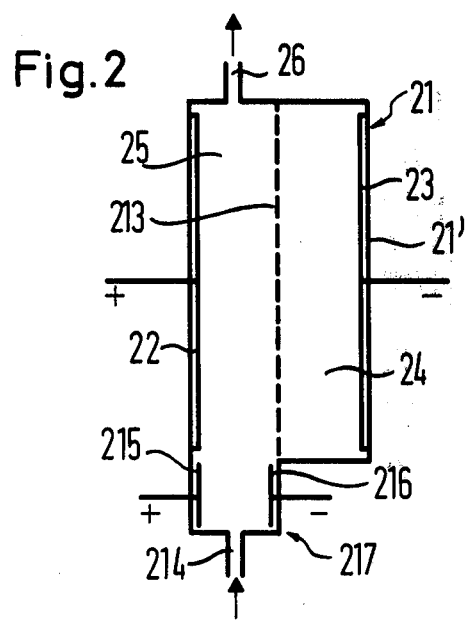

United States Patent [19]

Eibl

[11] 4,048,032
[45] Sept. 13, 1977

[54] ELECTROLYTIC PURIFICATION OF AQUEOUS LIQUIDS IN THE PRESENCE OF SILVER IONS

[75] Inventor: Volker Eibl, Munich, Germany

[73] Assignee: Sachs-Systemtechnik GmbH, Schweinfurt am Main, Germany

[21] Appl. No.: 608,244

[22] Filed: Aug. 27, 1975

[30] Foreign Application Priority Data

Sept. 3, 1974  Germany .............................. 2442078

[51] Int. Cl.² .......................... C02B 1/82; C02B 3/00
[52] U.S. Cl. ..................................... 204/151; 204/130; 204/149
[58] Field of Search ............... 204/149, 151, 212, 130; 426/322, 323, 301

[56] References Cited

U.S. PATENT DOCUMENTS

| | | | |
|---|---|---|---|
| 1,131,067 | 3/1915 | Landreth | 204/149 |
| 2,839,463 | 6/1958 | Vellas et al. | 204/212 |
| 3,192,146 | 6/1965 | Vellas et al. | 204/149 X |

Primary Examiner—Arthur C. Prescott
Attorney, Agent, or Firm—Hans Berman

[57] ABSTRACT

Silver ions are used more economically in the electrolytic purification of water by anodic oxidation when the water is electrolyzed between inert electrodes, and the silver ions are generated by separate silver anodes, than by employing the silver anodes also for generating oxygen.

4 Claims, 8 Drawing Figures

ELECTROLYTIC PURIFICATION OF AQUEOUS LIQUIDS IN THE PRESENCE OF SILVER IONS

This invention relates to the purification of aqueous liquids by anodic oxidation in the presence of silver ions, and particularly to a method of purifying an aqueous liquid of oxidizable contaminants and to an apparatus for performing the method.

It is known from the commonly owned application Ser. No. 473,389, filed May 28, 1974, and now U.S. Pat. No. 3,923,632 that the disinfecting action of electric current on water contaminated by microorganisms in the anode compartment of an electrolytic cell is enhanced by the presence of silver ions formed in the liquid from the silver anode employed.

While the amounts of silver required in the known method are small, the recent rapid rise in the cost of silver limits the application of the method to instances in which the taste of chlorine or of other, cheaper disinfectants is not acceptable.

It has now been found that the amount of silver required to be present in the anode area of an electrolytic cell for enhancing the anodic destruction of microorganisms is much smaller than that unavoidably discharged into the liquid from a silver anode operating under adequate oxidizing conditions, and that equally good results can be achieved by dosing the liquid with fewer silver ions independently from the electrolysis of the water.

According to the method of the invention, electrolyzing current is passed in an electrolyzing zone between an anode and a cathode through the liquid in which oxidizable contaminants are to be destroyed. Silver ions are added to the liquid before it is subjected to the passing of the current, and the magnitude of the current and the amount of added silver ions are separately controlled. The silver ions may be added to the liquid in the form of ionizable silver salts of acids which are nontoxic in the minute amounts involved, such as the sulfate, but are more conveniently formed in the liquid by electrolysis between an auxiliary silver anode and a negatively charged counterelectrode. In either case, only a small fraction of the total added silver is consumed in the disinfecting process, and it is often economically sound to recover the excess by the passage of electric current after the anodic oxidizing step and outside the main electrolyzing zone.

The apparatus employed, in its basic aspects, comprises a main electrolytic cell which includes a vessel, and an anode and a cathode, which define therebetween an electrolyzing zone in the vessel. A supply conduit and a discharge conduit communicate with respective spaced portions of the zone for flow of the liquid to be purified from the supply conduit to the discharge conduit through the zone. The anode and cathode are conductively connected to respective sources of a source of electric current. The material of the anode and cathode are selected to be chemically inert to the liquid during passage of the current through the liquid in the electrolyzing zone. A proportionating pump may be employed to supply a silver salt solution to the liquid entering the electrolyzing zone, and may be coupled by an electric circuit with a flow meter for the liquid to maintain a constant silver ion concentration in the electrolysis zone. It is generally more convenient to enrich the electrolyte with silver ions by means of an auxiliary electrolyzing circuit for passing electric current between a silver anode and a counterelectrode.

Other features, additional objects, and many of the attendant advantages of this invention will readily become apparent from the following detailed description of preferred embodiments when considered with the appended drawing in which:

FIG. 1 shows apparatus of the invention for anodically disinfecting drinking water in semi-diagrammatic top elevation; and FIGS. 2 to 8 illustrate respective modifications of the apparatus of FIG. 1 in corresponding views.

Referring initially to FIG. 1, there is shown a main electrolytic cell 1 which includes a vessel 1' having rectangularly offset walls of insulating material, such as glass or plastic. An anode 2 and a cathode 3 are sealed to respective opposite, flat walls of the vessel 1' so that only the flat, opposite, parallel faces of the two electrodes are exposed to liquid in the vessel. The electrodes are connected to the positive and negative terminals of a rectifier, as indicated by + and − signs, and the applied voltage may be controlled by an autotransformer at the rectifier in a manner conventional in itself and not shown.

A cathode compartment 4 partly bounded by the cathode 3, and an anode compartment 5 similarly bounded by the anode 2, are partitioned from each other by a semi-permeable membrane 14 which permits passage of current, but impedes mixing of the anolyte in the compartment 5 with the catholyte in the compartment 4.

The purified liquid is released from the anode compartment 5 through a discharge conduit 6 at the same rate at which liquid to be treated is admitted to the cell 1 by a conduit 7 integral with the discharge conduit 8 of an auxiliary cell 12 to constitute a connecting conduit of restricted flow section between the cells 1, 12.

Raw water is fed to the auxiliary cell 12 through a supply conduit 9, and electric current passes through the supplied water in the cell 12 between a silver anode 10 and a counterelectrode 11. The electrodes 2, 3, and 11 consist of material which is chemically inert and remains inert to the treated liquid and insoluble therein during passage of current through the two cells, austenitic stainless steel of AISI Type 316 being eminently suitable, but many other materials being available. Unless specifically stated otherwise, all electrodes described hereinbelow consist of such stainless steel. The electrodes 10, 11 of the auxiliary cell 12 are supplied with direct current through a circuit which permits adjustment of the voltage between the electrodes 10, 11 independent from the cell voltage between the electrodes 2, 3. A separate rectifier has been used for this purpose or a circuit connecting both cells 1, 12 to the same rectifier was equipped with independent variable resistors for each cell. The liquid in the connecting conduit 7, 8 is too poor a conductor to interfere with independent control of the two cell voltages and of the currents passing through the two cells respectively.

If two separate rectifiers are employed, the main cell and the auxiliary cell need not be separated by a liquid bridge of low conductivity. In the modified apparatus shown in FIG. 2, a single plastic vessel 21' encloses both the main cell 21 and the auxiliary cell 217 which is an integral appendage of the anode compartment 25. The silver anode 215 and the main stainless anode 22 are pieces of sheet metal closely juxtaposed in a common plane so that liquid flows sequentially from a supply conduit 214 along the anode faces to a discharge conduit 26. The counterelectrode 216 of the auxiliary cell 217 is exposed to the flowing liquid whereas the cathode 23 in the cathode compartment 24 of the main cell 21 is separated from the anode compartment by a diaphragm 213.

Figure 3:
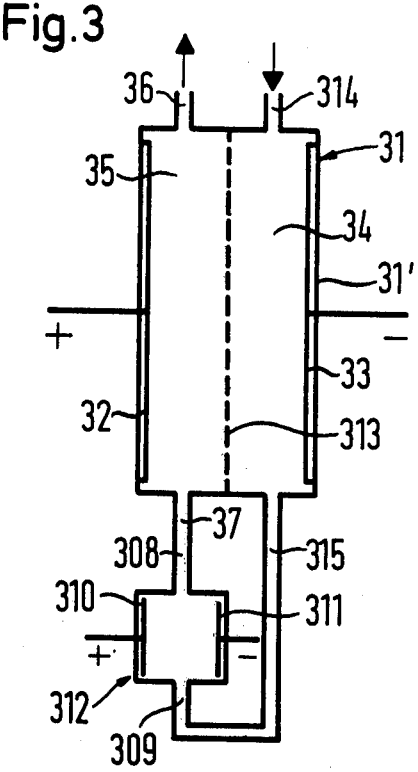

Since the liquid in the cathode compartment also undergoes electrolysis, and hydrogen deposited on the cathode may polarize the latter and raise the voltage needed for desired current flow, the apparatus of FIG. 1 may also be modified in the manner shown in FIG. 3 in which the entire liquid to be purified first enters the cathode compartment 34 of the main cell 31 through a supply conduit 314, and flows between the cathode 33 and a parallel diaphragm 313 preferentially permeable to anions to leave the main cell vessel 31' through a restricted conduit 315 which leads to the entrance port 309 of the auxiliary cell 312. Having been enriched with silver ions between a silver anode 310 and a counterelectrode 311, the liquid passes from the discharge conduit 308 of the auxiliary cell 312 and the entrance conduit 37 of the main cell 31 into the anode compartment 35 of the latter for oxidation of its microbial contaminants during passage between the anode 32 and the diaphragm 313 to a discharge conduit 36.

Figure 4:
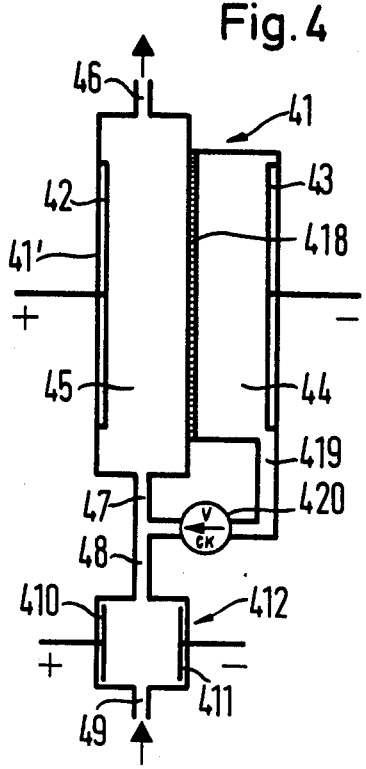

If it is inconvenient to pass the entire liquid to be purified through the cathode compartment of the main cell, the arrangement shown in FIG. 4 may be chosen in which the cathode compartment 44 of the main cell 41 is separated from the anode compartment 45 by an apertured plastic screen 418 which impedes, but does not prevent, liquid flow between the two compartments. The liquid to be purified between the main anode 42 and the main cathode 43 is supplied to the auxiliary cell 412 having a silver electrode 410 and a negative, stainless steel counterelectrode 411 through a conduit 49. A feedback conduit 419 leads from the cathode compartment 44 to a T-junction between the two longitudinal portions 47, 48 of a connecting conduit through which the silver-enriched raw water flows from the auxiliary cell 412 to the main cell 41.

The suction effect of the flowing raw water draws liquid from the cathode compartment 44 into the T-junction, and a check valve 420 in the conduit 419 prevents entrance of raw water into the cathode compartment 44 in which contaminating microorganisms may proliferate unchecked. A small amount of anolyte is continuously drawn through the screen 418 and suffices to keep the catholyte fresh and to control cathode polarization. The conduit 419 also increases average dwell time of the water in the cell 41. The purified water is released from the anode compartment through a discharge conduit 46.

Figure 5:
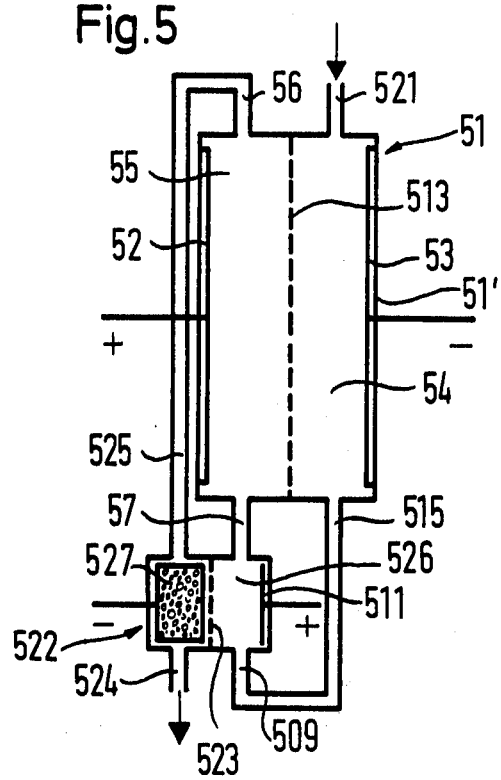

Although the amount of silver ions in the water treated in the apparatus of FIG. 3 may be held to a minimum by suitable control of the two cell voltages without reducing the disinfecting effect of the apparatus, it may be economically sound to recover such silver traces, and the modified apparatus illustrated in FIG. 5 is useful for this purpose.

As described with reference to FIG. 3, raw water enters the cathode compartment 54 of the main cell 51 through a supply conduit 521, passes between the cathode 53 and the diaphragm 513 of the cell, and is transferred from the vessel 51' of the main cell to the entrance port 509 of an auxiliary cell 522 through a connecting conduit 515. The modified auxiliary cell 522 employed in the apparatus of FIG. 5 is divided into anode and cathode compartments by a diaphragm 523 of ion exchange material which does not permit microorganisms nor silver ions to pass between the compartments. The raw water entering the anode compartment 526 is enriched with silver ions from a silver anode 511, and flows through a connecting conduit 57 into the anode compartment 55 of the main cell 51 for destruction of microbes during flow along the exposed face of the anode 52. The purified water leaving the vessel 51' through a discharge port 56 is returned to the auxiliary cell 522 by a conduit 525 for exposure to the cathode 527 of the auxiliary cell before being released through a discharge conduit 524. The cathode 527 has a large effective surface and is recessed for trapping silver-bearing solids which are precipitated cathodically from the purified water. Recovery of the silver values from the precipitate is particularly convenient when the cathode consists of combustible plastic fabric made conductive by a graphite film, but steel wool and coarse, sintered, other base metals also provide cathodes from which silver may be recovered by selective destruction of the cathode or by selective dissolution of the silver-bearing precipitate.

Figure 6:
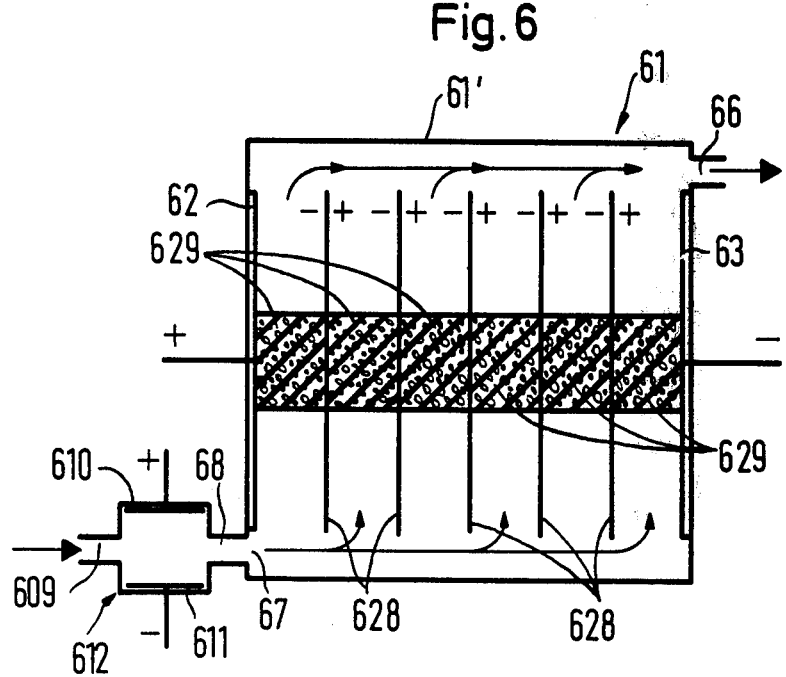

A large effective anode area in a small space is provided by the embodiment of the invention shown in FIG. 6 in which the main cell 61 has a vessel 61' whose height, width, and length are closely similar. Two opposite walls are covered by a flat, sheet metal cathode 62 and an anode 63 of similar material which are spaced apart in parallel relationship. Cylindrical spacers 629 of insulating material secure a stack of five circular, stainless steel plates 628 in uniformly spaced relationship between the electrodes 62, 63 so that the two major faces of each plate 628 are parallel to the exposed faces of the electrodes 62, 63. When voltage is applied to the electrodes 62, 63, the two faces of each plate 628 become negative and positive respectively and act as anodes and cathodes on the silver-ion bearing liquid flowing between the electrodes 62, 63 and the plates 628 which constitute bipolar electrodes.

The liquid is enriched with silver ions before treatment in the main cell 61 by entering an auxiliary cell 612 through a supply conduit for exposure to direct current between a silver anode 610 and a stainless steel counterelectrode 611, and leaves the auxiliary cell 612 through a conduit 68. It flows through the main cell 61 from an entrance port 67 diagonally to a discharge port 66, being diverted by the bipolar electrodes 628 into paths parallel to the electrode faces.

A membrane or semi-permeable partition separating the anode and cathode compartments in an electrolytic cell according to the invention is usually preferred to avoid or reduce the mixing of anolytes and catholytes which may cause the loss of anodically produced, antimicrobial oxidizing agents, such as peroxides, chlorites, or ozone, and the precipitation of a silver-bearing sludge in the main cell. However, the importance of these secondary effects is decreased as the linear velocity of the treated liquid in the main cell increases, and the provision of a dividing membrane has not been found necessary in the apparatus of FIG. 6.

Figure 7:
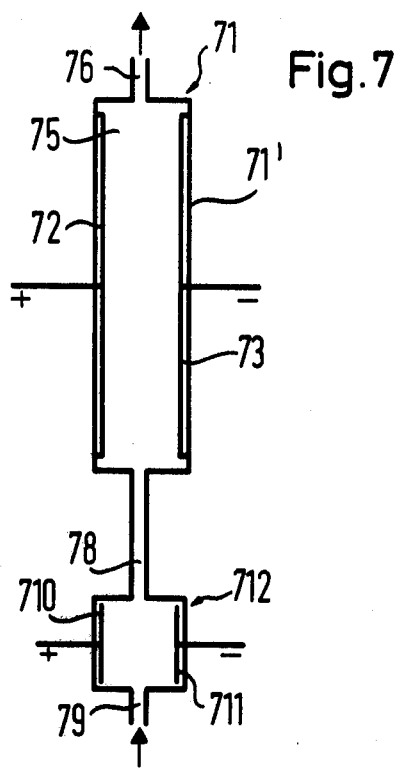

Actually, apparatus not very different from that described above with reference to FIG. 1 may be operated successfully without separation of anode and cathode compartments, and such modified apparatus is shown in FIG. 7. An auxiliary cell 712 and a main cell 71 are arranged for series flow of liquid from a supply conduit 79 through the enriching zone of the cell 712 between a silver anode 710 and a stainless steel counterelectrode 711, through a restricted conduit 78 into the undivided cavity 75 of the main cell casing 71' in which an anode 72 faces a cathode 73, the treated water being released through an outlet 76 of the cell 71. The transverse dimension of the flow path between the electrodes 72, 73 is similar to that between the anode 2 and the diaphragm 13 in the apparatus of FIG. 1 to keep the entire flowing liquid within effective range of the oxidants generated at the anode 72.

Figure 8:
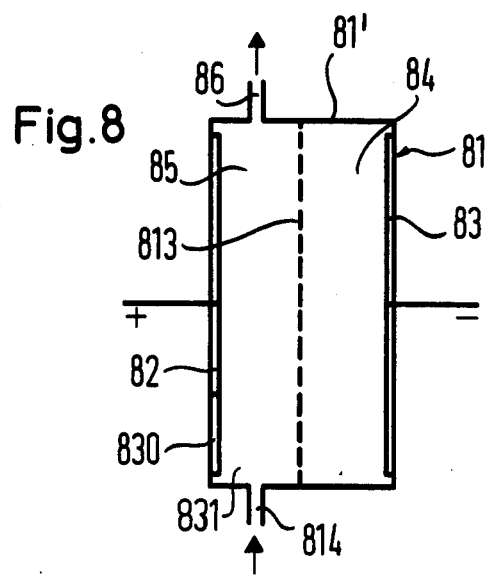

Even if separate external circuits are not available for energizing the electrodes of the main cell and of the auxiliary cell, the ratio between silver dissolution and oxidizing effect can be controlled independently at least to some effect in the manner shown in FIG. 8. The vessel 81' of a cell 81 is divided into an anode compartment 85 and a cathode compartment 84 by a diaphragm or membrane 813, and the water to be purified is pumped through the anode compartment from an inlet 814 to an outlet 86 in a path parallel to the membrane 813 and to a stainless steel cathode 83 which almost completely covers a wall of the cathode compartment 84. The corresponding wall of the anode compartment carries a silver anode 830 near the inlet 814 and a stainless steel anode 82 extending from the silver anode 830 in a common plane toward the outlet 86.

While the silver and stainless steel anodes 830, 82 are conductively directly connected and mechanically fixedly attached to each other, polarisation effects and the differences between the anodic dissolution potential of silver and the anodic decomposition potential of water produce a current distribution between the two anodes 82, 830 which may be controlled by selecting or varying the exposed anode areas, as by masking with tape or lacquer. The very simple arrangement shown in FIG. 8 is of greatest advantage for long-term operation of water treating equipment under reasonably constant conditions. The greatest concentration of silver ions is found in the area 831 adjacent the silver anode 830 in the compartment 85, and the silver ions are carried by the flowing water into the electrolyzing zone defined between the stainless steel anode 82 and the cathode 81, an integral portion of which functions as a counterelectrode to the silver anode 830. Because of the small amounts of silver dissolved during operation of the apparatus illustrated in FIG. 8, the separate, fixedly attached silver anode 830 may be replaced by a rolled or galvanically deposited surface coating of silver on the exposed face of the stainless steel anode 82.

The following Examples illustrate the operation of the apparatus of the invention.

EXAMPLE 1

In an actual embodiment of the device shown in FIG. 3, the distance between the exposed anode face and the membrane 313 was 4 mm. The numerical values of the exposed anode area F (in cm$^2$) and of the flow rate of water $\dot{v}$ (in cm$^3$/sec.) through the anode compartment 35 were so chosen that $F/\dot{v} = 5$. The main cell voltage was adjusted as needed to maintain an anode current density of 2.7 mA per cm$^2$ anode surface.

The specific resistivity of the treated water was 2400 ohm.cm. The membrane 313 was a commercial product employed for dialysis and consisting of regenerated cellulose. The auxiliary cell voltage was maintained at a value to dissolve 1 mg silver from the anode 310 for each liter of water passing through the apparatus.

The contaminated drinking water contained 10$^7$ viable microorganisms per ml prior to treatment. Its average dwell time in the anode compartment 35 was 4 seconds, and the number of viable microbes in the treated water was reduced to 0.57% of the initial value.

EXAMPLE 2

The apparatus employed was of the general type shown in FIG. 6, but is was equipped with 56 bipolar electrodes. Each electrode had an area of 95 cm$^2$ so that the total bipolar anode area was 5,320 cm$^2$. The directly energized electrodes and the bipolar electrodes defined flow paths having a uniform width of 2 mm, and the raw water was pumped through the main cell at a rate of 2.2 liters per minute (37 cm$^3$/sec.). The silver anode 610 in the auxiliary cell was controlled at a metal loss of 0.1 mg silver per liter of treated liquid by adjusting the applied potential.

The water fed to the auxiliary cell 612 contained 8.62 $\times$ 10$^6$ viable microbes. The average dwell time in the main cell was 29 seconds. The treated water was practically free from viable microorganisms.

EXAMPLE 3

In an apparatus of the type shown in FIG. 6 having seven bipolar electrodes of 95 cm$^2$ anode area set 2 mm apart, contaminated water was treated at a rate corresponding to the relationship $F/\dot{v} = 30$, wherein F is the numerical value of the total anode area in cm$^2$, and $\dot{v}$ is the numerical value of the flow rate in cm$^3$/sec. An anode current density of 8 mA/cm$^2$ was maintained by controlling the voltage across the electrodes of the main cell, and the voltage across the auxiliary cell was selected to produce a weight loss of 0.33 mg silver from the silver anode 610 per liter of treated water.

The raw water fed to the silver-enriching zone contained 10$^8$ live microorganisms per ml, the average dwell time in the main electrolyzing zone was 6 seconds, and the treated water was free of viable microorganisms.

The microorganisms initially found in total plate counts of the contaminated water processed in Examples 1 to 3 were mainly Escherichia coli. No attempt was made at identifying all species present, particularly in view of the fact that they responded equally well to the electrolytic treatment.

While it is desirable that the electrode faces exposed to the treated liquid be smooth in the direction of liquid flow, they need not be planar as specifically illustrated in the drawing. Cylindrical, coaxial electrodes have been found to be equally effective and may be preferred under conditions not encountered in this work so far.

It should be understood, therefore, that the foregoing disclosure relates only to preferred embodiments, and that it is intended to cover all changes and modifications of the examples of the invention herein chosen for the purpose of the disclosure that do not constitute departures from the spirit and scope of the invention set forth in the appended claims.

What is claimed is:

1. A method of destroying oxidizable contaminants in an aqueous liquid which comprises:
   a. adding silver ions to said liquid in a first zone;
   b. conveying said liquid from said first zone to a second zone;
   c. passing electrolyzing current through said liquid in said second zone in the presence of said silver ions and said contaminants between an anode and a cathode, said anode being in direct contact with said liquid and insoluble in said liquid during said passing of said current;

d. independently controlling the magnitude of said current and the amount of said silver ions to respective values jointly sufficient to destroy said contaminants in said second zone; and e. withdrawing said liquid in purified condition from said second zone.

2. A method as set forth in claim 1, wherein said silver ions are added to said liquid by passing another electric current between a silver anode and a counterelectrode through said liquid, and the amount of the silver ions added by said passing of the other electric current is controlled by controlling the magnitude of said other current.

3. A method as set forth in claim 2, which further comprises passing depositing current through said purified liquid and thereby precipitating silver values from said liquid outside said second zone.

4. A method as set forth in claim 2, wherein said liquid is fed continuously to said first zone and withdrawn continuously from said second zone, whereby a continuous sequential flow of liquid is maintained through said zones, said liquid being conveyed from said first to said second zone through a conduit having a smaller flow section than the flow section of each of said zones.

* * * * *